US00PP20176P3

(12) United States Plant Patent
Dirr

(10) Patent No.: US PP20,176 P3
(45) Date of Patent: Jul. 7, 2009

(54) ***HYDRANGEA MACROPHYLLA* PLANT NAMED 'PIIHM-1'**

(50) Latin Name: *Hydrangea macrophylla*
Varietal Denomination: PIIHM-1

(75) Inventor: Michael Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 59 days.

(21) Appl. No.: 11/999,784

(22) Filed: Dec. 7, 2007

(65) Prior Publication Data

US 2009/0151033 P1 Jun. 11, 2009

(51) Int. Cl.
*A01H 5/00* (2006.01)

(52) U.S. Cl. ..... Plt./250

(58) Field of Classification Search ..... Plt./250
See application file for complete search history.

(56) References Cited

PUBLICATIONS

A New Reblooming Lacecap *Hydrangea macrophylla*; Brochure hand–out at Lantana and Hydangea trade show, Aug. 2007.

*Primary Examiner*—Kent L Bell
(74) *Attorney, Agent, or Firm*—Greenlee Winner and Sullivan, PC

(57) ABSTRACT

A new and distinct cultivar of *Hydrangea macrophylla* plant named 'PIIHM-I', characterized by its upright, rounded and spreading growth habit; remontant flowering (reblooming, flowers on new growth); bright pink lacecap inflorescences; dark green, powdery mildew resistant foliage, orange to rich rose-red to red-purple fall color; and pink-red stems.

7 Drawing Sheets

Genus and species of plant claimed: *Hydrangea macrophylla* (Thunb.) Ser.
Variety denomination: 'PIIHM-I'.

BACKGROUND OF THE INVENTION

The present invention relates to a new and distinct cultivar of *Hydrangea macrophylla,* a member of the Hydrangeaceae family, hereinafter referred to by its cultivar name 'PIIHM-I'. This cultivar is grown primarily as an ornamental for landscape use and for use as a potted plant. The cultivar originated from controlled cross-pollination of *Hydrangea macrophylla* 'Penny Mac' (unpatented) by *Hydrangea macrophylla* 'Lady in Red' (U.S. Plant Pat. No. 15,175) in Athens, Ga. in 2003, and was selected from the progeny seedlings of this cross by continued evaluation for reblooming, increased resistance to mildew, and improved leaf and flower characteristics.

'PIIHM-I' has been asexually reproduced by softwood cuttings since 2004 in Athens, Ga. and in Watkinsville, Ga. The characteristics of the cultivar have been stable and reproduced true to type in successive vegetative generations.

'PIIHM-I' is distinguished from its female parent 'Penny Mac' by its lacecap inflorescence, flower color, foliage color, fall color, stem color, and its increased resistance to powdery mildew, and from its male parent 'Lady in Red' by its reblooming trait, flower color, and stem color. 'PIIHM-I' has bright pink lacecap inflorescences in non-aluminum media and pink-purple inflorescences in aluminum media, whereas 'Penny Mac' and 'Lady in Red' produce pink inflorescences in non-aluminum media and blue inflorescences in aluminum media. 'PIIHM-I' has thicker, darker green leaves than 'Penny Mac'. The leaves of 'PIIHM-I' develop orange to rich rose-red to red-purple fall color whereas leaves of 'Penny Mac' turn yellow or senesce green to brown.

'PIIHM-I' has pink-red stems, whereas 'Penny Mac' has green stems and 'Lady in Red' has red stems. There are no other reblooming cultivars of *Hydrangea macrophylla* with bright pink lacecap inflorescences known to the inventor.

SUMMARY OF THE INVENTION

'PIIHM-I' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIHM-I' from all other varieties in commerce known to the inventor. 1) Remontant (reblooming) trait, flowering on old wood and new growth of the season. 2) Bright pink lacecap inflorescences or pink-purple inflorescences in non-aluminum or aluminum based media, respectively. 3) Upright, rounded and spreading growth habit. 4) Dark green foliage. 5) Orange to rich rose-red to red-purple fall color. 6) Powdery mildew resistant foliage. 7) Pink-red stems.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea.*

DETAILED DESCRIPTION

Figure 1:
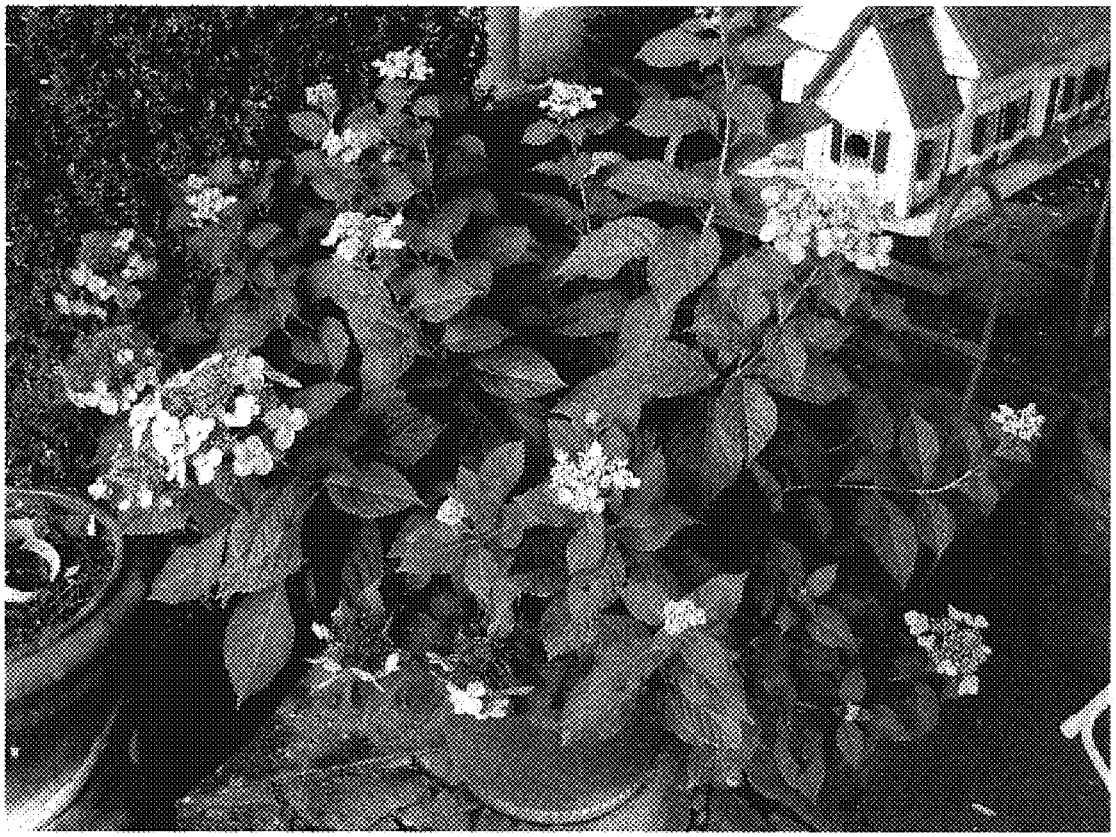
FIG. 1 shows a three-year-old 'PIIHM-I' plant grown without aluminum.
Figure 2:
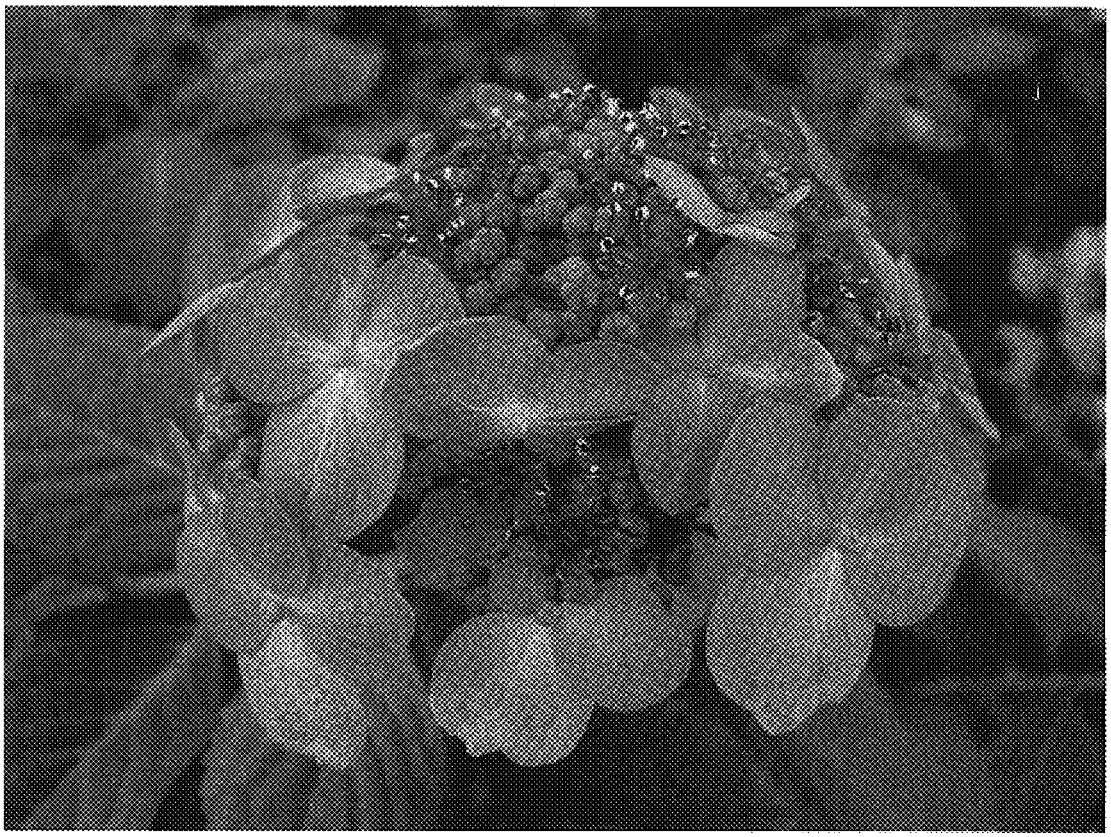
FIG. 2 shows inflorescence on a 'PIIHM-I' plant grown in absence of aluminum.
Figure 3:
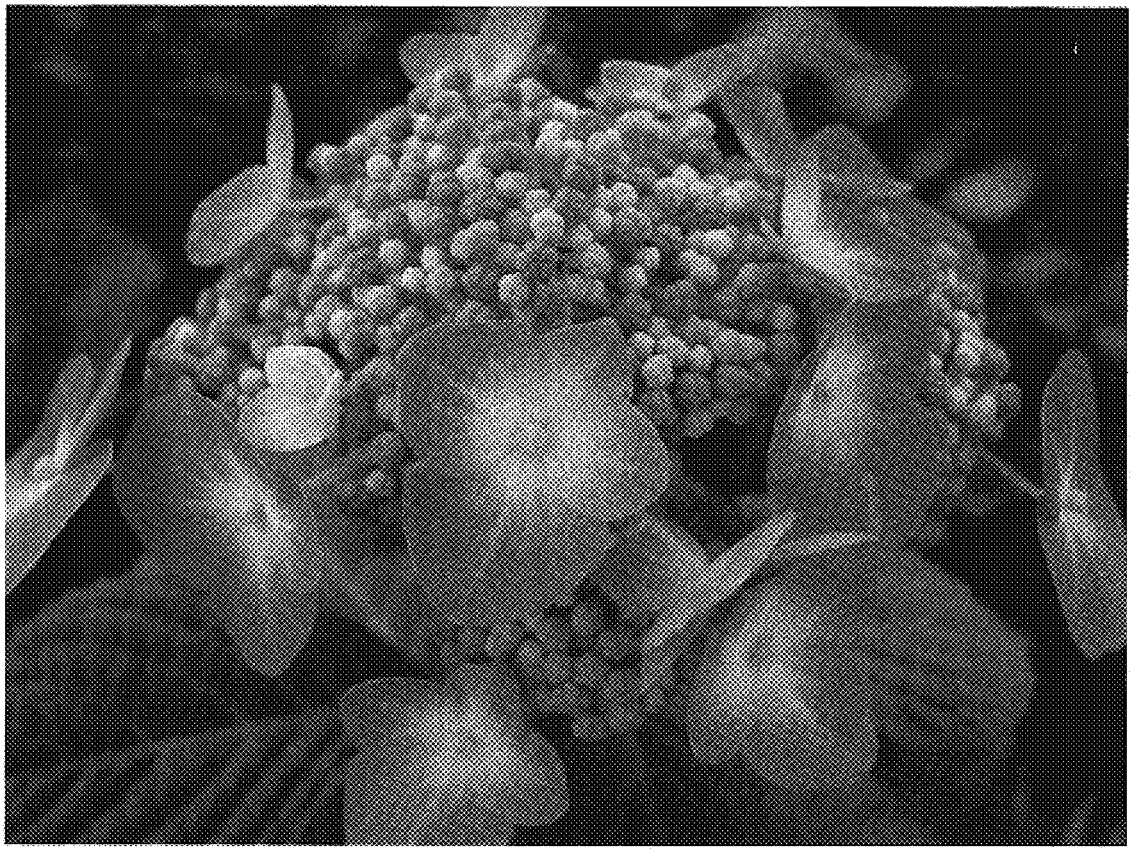
FIG. 3 shows developing inflorescence on plant grown without aluminum.
Figure 4:
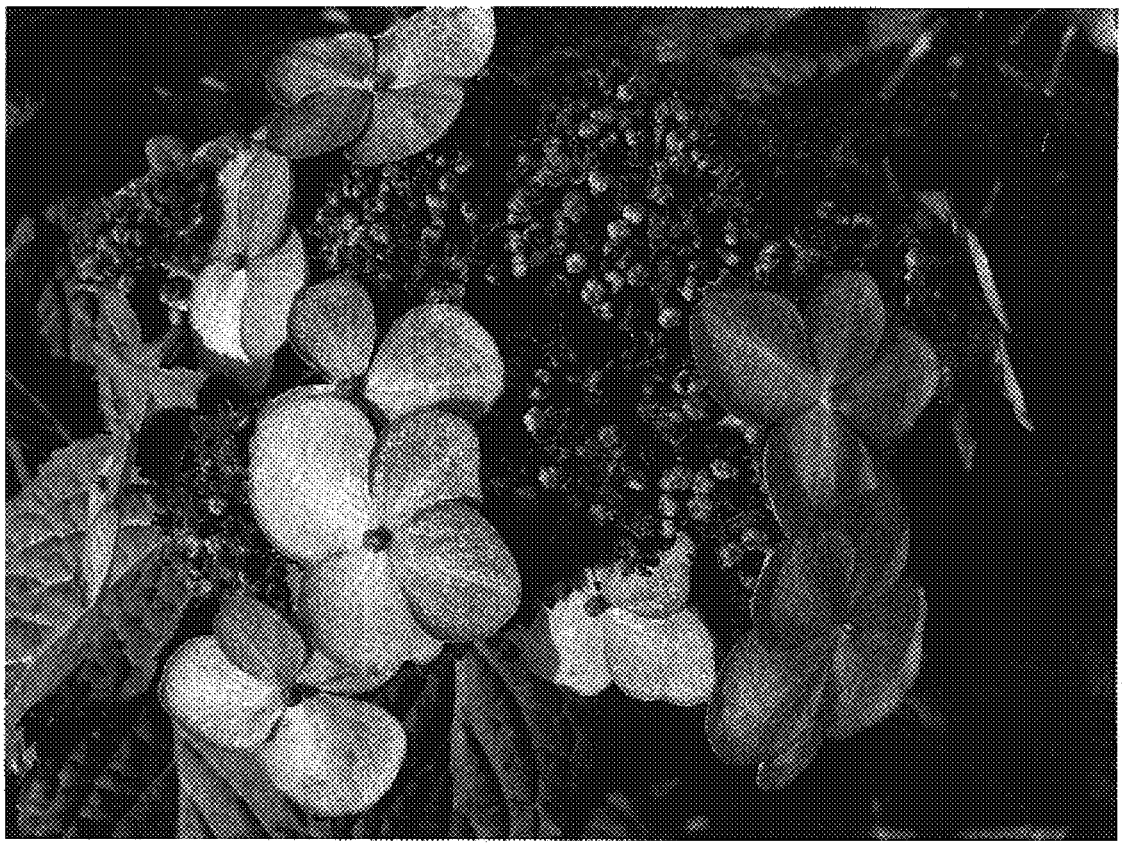
FIG. 4 shows inflorescence of a 'PIIHM-I' plant maturing to pink-purple on plant growing in presence of aluminum.
Figure 5:
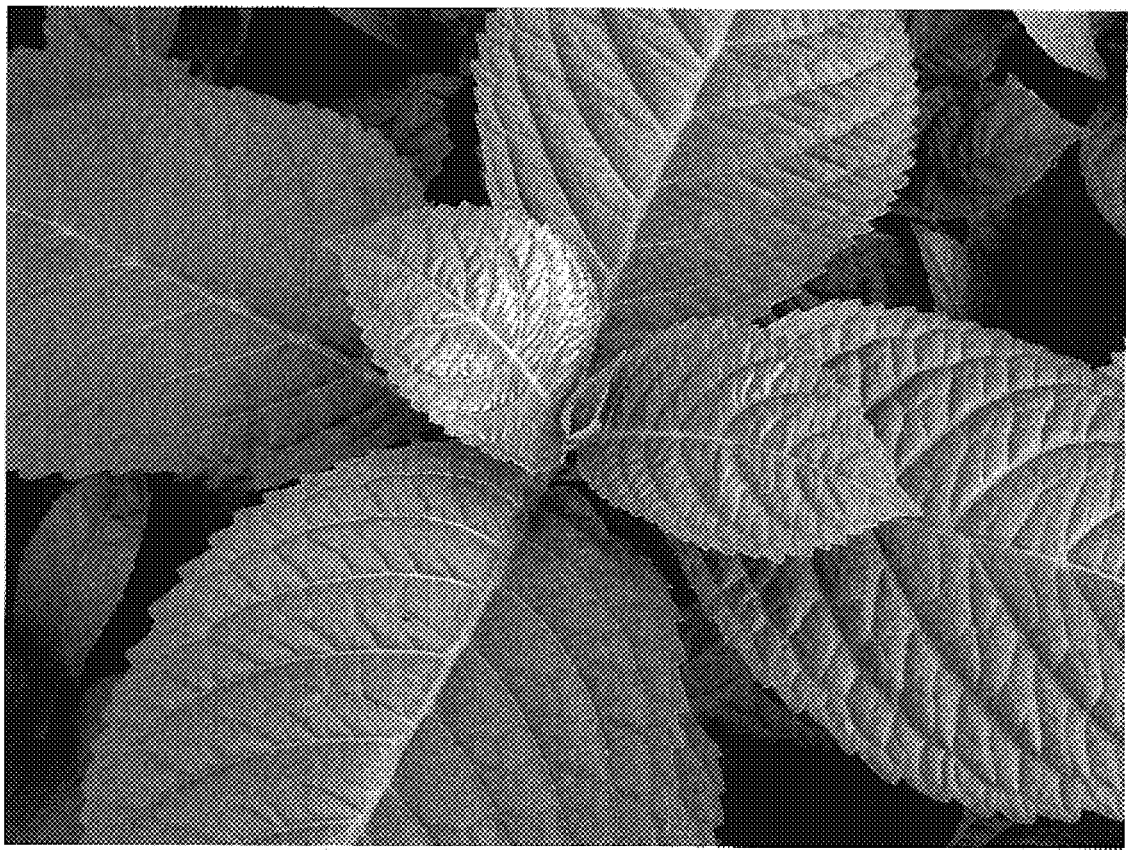
FIG. 5 shows a close up of mature foliage in summer.
Figure 6:
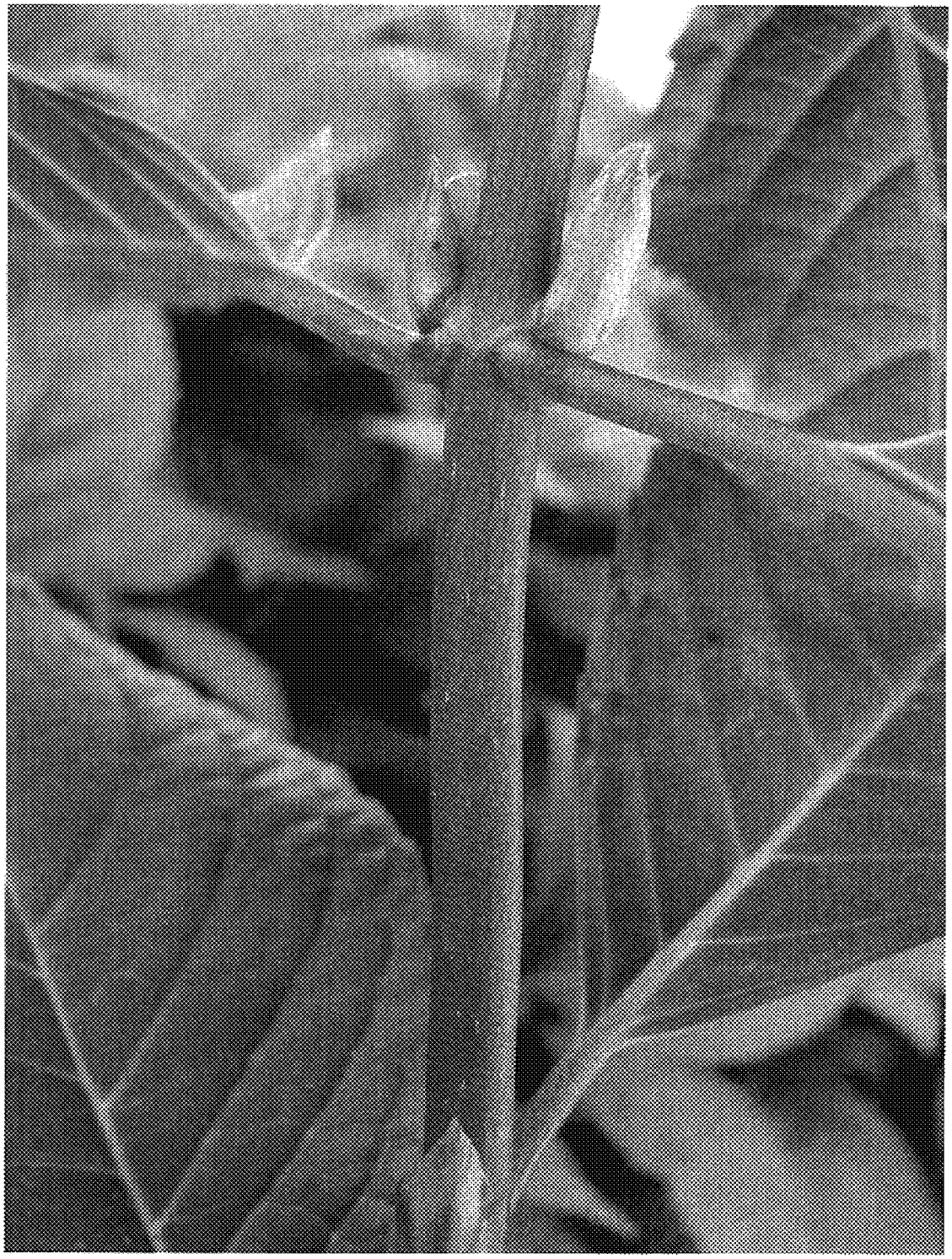
FIG. 6 shows a close up of a stem of a 'PIIHM-I' plant.
Figure 7:
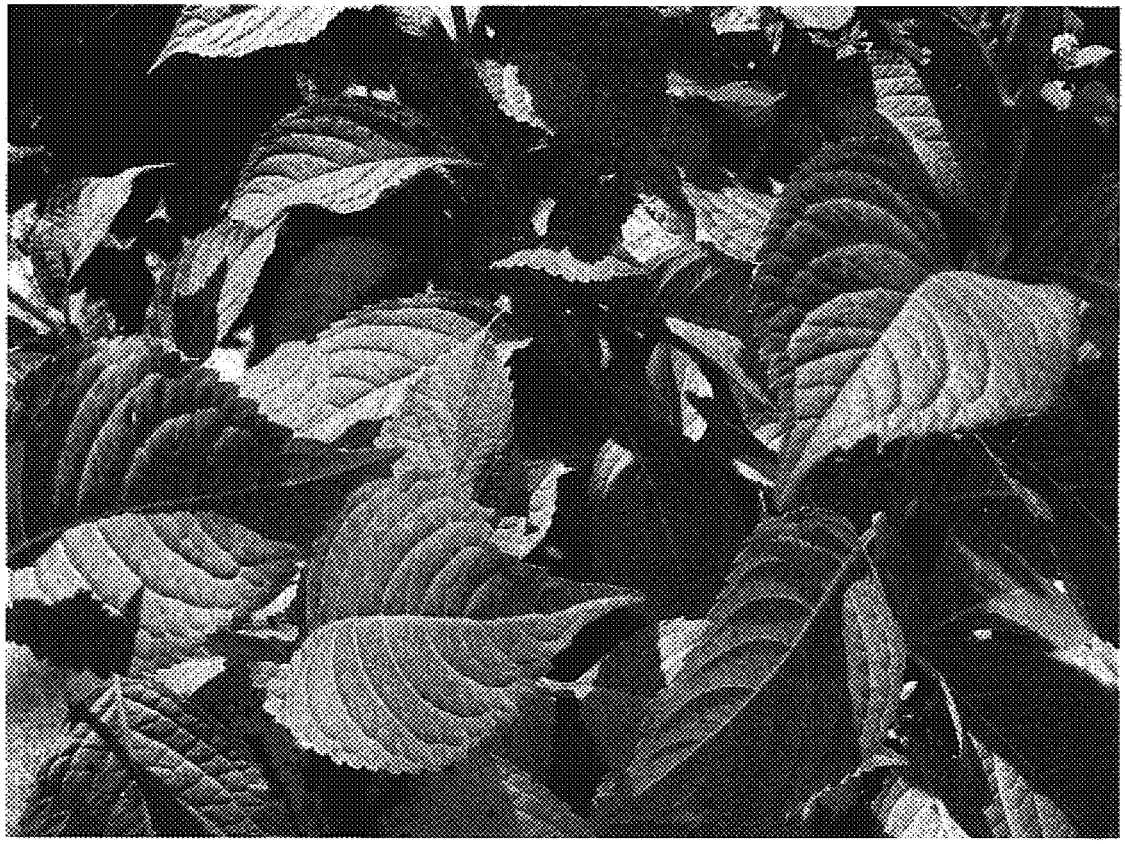
FIG. 7 shows foliage of a 'PIIHM-I' plant showing development of fall colors.

In the following description, color references are made to The Royal Horticultural Society Colour Chart, 2001 Edition, except where general terms of ordinary dictionary significance are used. Plants used for the description were grown in 27 L containers under 50% shade under outdoor conditions in a nursery in Watkinsville, Ga. Plants were about 2½ years old when the description was recorded. To determine the influence of aluminum on flower color, 42 grams of aluminum sulfate were added to the medium surface when inflorescences were just visible, green, with cauliflower-shaped buds.

Botanical classification: 'PIIHM-I' is a cultivar of *Hydrangea macrophylla*. Parentage: The current variety is a progeny from a *Hydrangea macrophylla* 'Penny Mac'×'Lady in Red' controlled cross. Propagation: Vegetatively by stem cuttings.

PLANT DESCRIPTION

The claimed variety is an upright, rounded and spreading deciduous shrub. About 81 cm high, 101 cm wide. Freely branching. Branches range in length from about 20 to 50 cm. The plant has a hardiness in USDA Zones 5 to 9.

Stems: First year stems have a diameter of about 4 mm, a round shape, and a stout, glabrous, lustrous texture. Pubescence — none. Exfoliation — on second year stems, flaky and stringy. Internodes have a length of about 4.6 cm. The stem color is close to 144A, maturing close to 182A. Second year stems have a diameter of about 6 mm and color close to N199C.

Vegetative buds: Arrangement — opposite; Shape — ovoid; Size — about 2 mm in length, about 1 mm in width; Color — close to 144A, maturing close to 182A.

LEAVES

*Size.*—About 8.8 cm in length and about 5.5 cm in width. Shape — ovate, with acuminate apex, cuneate base and serrate margin. Texture — thick and leathery. Color — emerging leaves are close to 144A on the upper surface and close to 146B on the lower surface; mature leaves on the upper surface are close to 139A, and close to 137A on the lower surface; fall leaves develop a range of colors from orange to rose-red to red-purple.

*Venation.*—Pinnate, veins are close to 144B.

*Petiole size and shape.*—About 8 mm in length and about 2 mm in diameter, glabrous. Petiole color — close to 176A.

FLOWER DESCRIPTION

*Flower bud size.*—About 3 mm in length, about 3 mm in width, and about 3 mm in depth. Flower bud shape — round; Color — close to 84B when grown with aluminum, and close to 75A when grown without aluminum.

*Inflorescence bloom period.*—Early summer to first frost in fall. An inflorescence contains about 380 individual fertile flowers. Inflorescence shape and size — lacecap, about 15 cm in length and about 15 cm in width. The inflorescence is effective for about 8 weeks. The peduncle averages about 1.2 cm in length, is finely pubescent and is close to N80B with aluminum and close to 179B without aluminum. Sterile florets contain 4 sepals about 1.9 cm in length and about 1.7 cm in width. An inflorescence contains about 23 individual sterile florets. Sterile floret shape — ovoid with obtuse apex, acute base, and entire margin; Texture — smooth with no pubescence; Color — with aluminum, the upper surface is close to N81C and the lower surface is close to N82D at peak flowering. Without aluminum, the upper surface is close to 71D and lower surface is close to N74D at peak flowering.

Petals (fertile flowers): Size — 5 petals per flower, about 3 mm in length and about 1 mm in width; Shape — ovate, with acuminate apex, truncate base, and entire margin; Texture — smooth with no pubescence; color — at peak of bloom the upper surface of the petals is close to N81C and the lower surface is close to N81D with aluminum. When grown without aluminum the upper surface of the petals is close to N78C and the lower surface is close to N78D.

Number of Stamens: 5 to 6. Anthers — about 1 mm in length and about 0.5 mm in width, close to 95A with aluminum and close to 83C without aluminum. Filaments — about 3 mm in length and about 0.5 mm in width, close to N88A with aluminum and close to N78B without aluminum. Pollen — close to 155D. Pistil — superior, about 3 mm in length and about 1 mm in width, close to N82A with aluminum and close to N74C without aluminum. Stigma — 3 or 4 per pistil, round in shape and close to 86A with aluminum and close to N74B without aluminum. Style — about 2 mm in length and tubular in shape, close to 86B with aluminum and close to N74C without aluminum.

FRUIT

The capsule fruit is ovoid, about 3 mm in length and about 2 mm in width. The color during early ripening is close to 54B and at maturity is close to 200C. The number of fruit per infructescence varies widely. Seed: The seeds are round, about 0.5 mm in length and about 0.5 mm in width, close to 199B, and each capsule contains about 50 seeds.

DISEASE/PEST RESISTANCE

Excellent resistance to powdery mildew. No other pest or disease resistance/susceptibility has been observed.

I claim:

1. A new and distinct *Hydrangea macrophylla* plant named 'PIIHM-I', substantially as illustrated and described herein.

* * * * *